United States Patent [19]
Rullo et al.

[11] Patent Number: 6,090,042
[45] Date of Patent: Jul. 18, 2000

[54] SURGICAL SUPPORT APPARATUS WITH ADJUSTABLE RAKE AND ADJUSTABLE CABLE LIFTING DISK

[76] Inventors: Janice Lee Rullo, 1422 SOM Center Rd., Mayfield Heights, Ohio 44124; William John Koteles, 9002 Avery Rd., Broadview Heights, Ohio 44147

[21] Appl. No.: 09/235,172

[22] Filed: Jan. 22, 1999

Related U.S. Application Data

[60] Provisional application No. 60/072,366, Jan. 23, 1998, provisional application No. 60/072,240, Jan. 23, 1998, provisional application No. 60/072,273, Jan. 23, 1998, and provisional application No. 60/072,274, Jan. 23, 1998.

[51] Int. Cl.$^7$ .................................................. A61B 17/00
[52] U.S. Cl. .......................... 600/210; 600/227; 600/228
[58] Field of Search ..................................... 600/201, 210, 600/217, 227, 228, 235, 229, 231, 232

[56] References Cited

U.S. PATENT DOCUMENTS

| | | |
|---|---|---|
| 1,048,750 | 12/1912 | Smith . |
| 1,242,688 | 10/1917 | Hawley . |
| 1,914,202 | 6/1933 | Henze et al. . |
| 3,403,675 | 10/1968 | Carr . |
| 3,643,655 | 2/1972 | Peronti . |
| 3,710,783 | 1/1973 | Jascalevich . |
| 3,823,709 | 7/1974 | McGuire . |
| 4,143,652 | 3/1979 | Meier et al. . |
| 4,151,838 | 5/1979 | Crew . |
| 4,622,955 | 11/1986 | Fakhrai . |
| 4,627,421 | 12/1986 | Symbas et al. . |
| 4,702,465 | 10/1987 | McConnell . |
| 4,726,356 | 2/1988 | Santilli et al. . |
| 4,813,401 | 3/1989 | Grieshaber . |
| 4,829,985 | 5/1989 | Couetil . |
| 4,865,019 | 9/1989 | Phillips . |
| 5,025,779 | 6/1991 | Bugge . |
| 5,088,472 | 2/1992 | Fakhrai . |
| 5,109,831 | 5/1992 | Forrest et al. ........................ 600/228 |
| 5,545,123 | 8/1996 | Oritz et al. ........................... 600/235 |
| 5,613,939 | 3/1997 | Failla ................................. 600/210 X |
| 5,616,177 | 4/1997 | Dinkler et al. . |
| 5,667,481 | 9/1997 | Villalta et al. . |
| 5,803,903 | 9/1998 | Athas et al. ........................... 600/231 |

FOREIGN PATENT DOCUMENTS

| | | |
|---|---|---|
| 232451 | 12/1968 | Russian Federation . |
| 1210800 | 2/1986 | U.S.S.R. .............................. 600/228 |

OTHER PUBLICATIONS

Rultract Incorporated, Circulator Applied Internal Mammary Artery Retractor advertisement (undated).

Transaxillary Approach for First Rib Resection to Relieve Thoracic Outlet Syndrome, David B. Roos, M.D., from the Department of Surgery, University of Colorado School of Medicine, Annals of Surgery, Mar. 1966.

Thoracic Outlet Syndrome, David B. Roos, M.D. and J. Cuthbert Owens, M.D., Arch Surg—vol. 93, Jul. 1966.

KNY Scheerer Corp., Catalog of Surgical Instruments dated 1959, pp. 70–75 and 90–92.

The Surgical Armamentarium, V. Mueller, dated 1973, pp. 68, 281, 346, 347.

The Surgical Armamentarium, American V. Mueller, dated 1980, pp. 74, 75, 78, 87, 88.

Codman & Shurtleff, Inc., Catalog for Surgical Products dated 1984, pp. 431–437.

Copending U.S. application Ser. No. 09/235,704 filed on Jan. 22, 1999.

Stille Stainless Steel Retractors catalog dated Dec. 18, 1939.

*Primary Examiner*—Jeffrey A. Smith

[57] ABSTRACT

The present invention relates to a cable plate retractor assembly which includes a pivotable mounting plate to which a rake and a cable plate assembly are attached. The length of both the rake and the lifting plate portion of the cable plate assembly is threadably adjustable relative to the mounting plate. A method of retracting a portion of a patient's body adjacent a surgical cavity includes making a first surgical incision, placing a rake in a position for retraction, retracting a first portion of the patient's body with the rake, making a second surgical incision, inserting a first end of a cable with a lifting plate thereon into the surgical cavity, drawing the first end of the cable through the second incision whereby the lifting plate is retained in the patient's body at a second end of the cable, adjusting the position of at least one of the rake and the lifting plate relative to the mounting plate, and retracting a second portion of the patient's body by raising the lifting plate.

33 Claims, 4 Drawing Sheets

SURGICAL SUPPORT APPARATUS WITH ADJUSTABLE RAKE AND ADJUSTABLE CABLE LIFTING DISK

CLAIM FOR PRIORITY

This application claims priority under 35 U.S.C. 119(e) based on previously filed applications Ser. No. 60/072,366, Ser. No. 60/072,240, Ser. No. 60/072,273 and Ser. No. 60/072,274, all of which were filed Jan. 23, 1998, and all of which are incorporated herein by reference in their entirety.

CROSS-REFERENCE TO RELATED APPLICATIONS

Reference is hereby made to the following applications co-pending herewith, the disclosure of each of which is hereby incorporated by reference in its entirety: SURGICAL SUPPORT APPARATUS WITH SPECIALIZED RAKES, Ser. No. 60/072,366; SURGICAL SUPPORT APPARATUS WITH CROSS BAR SUPPORT AND EXTENSION FOR RETRACTOR APPARATUS, Ser. No. 60/072,240; SURGICAL SUPPORT APPARATUS WITH ADJUSTABLE RAKE AND ADJUSTABLE CABLE LIFTING DISK, Ser. No. 60/072,273; and SURGICAL SUPPORT APPARATUS WITH A Z-SHAPED RAKE PLATE, Ser. No. 60/072,274.

1. Field of the Invention

The present invention relates generally to surgical instruments for holding and elevating body parts and/or for maintaining a clear opening to a body area during surgery, particularly thoracic surgery. More specifically, the present invention relates to support apparatus upon which surgical devices, such as retractors and the like, may be operably mounted.

2. Background of the Invention

In the performance of surgery in the chest cavity, generally referred to as thoracic surgery, it is desirable to hold open the surgical cavity to provide access to the organ or body part upon which the surgery is being performed. This is especially important in the case of cardiac surgeries. An early example of a surgical retractor for use in coronary bypass surgical procedures which include dissection of the internal mammary artery is disclosed in U.S. Pat. No. 4,622,955, which is incorporated herein by reference.

In the device of U.S. Pat. No. 4,622,955 plural rakes which engage the body and retract the surgical cavity formed by a midsternotomy are relatively fixedly positioned with respect to each other from a rod. The rod may be elevated or lowered as desired. However, there is no adjustment for the rakes relative to the rod, to each other or to the surgical cavity. Furthermore, the rakes are generally small having sharply pointed tips and are generally designed to be employed in pairs for the purpose of retracting one side of a sternum which has been split by a midsternotomy. The device of U.S. Pat. No. 4,622,955 cannot provide the support required for other procedures which have been recently developed as alternatives to the midsternotomy approach to the coronary bypass, and it is not adapted for use in reoperative midsternotomy procedures.

It is well-known and appreciated that in surgical procedures, time is of the essence, and delays associated with adjustments of support equipment are unwanted. Additionally, during certain procedures, it may be desirable to impose or to change a biasing force on a body portion which is undergoing a surgical procedure or treatment. Further, it is desirable to minimize the number of personnel required to assist in the performance of a surgical procedure, to minimize the number of personnel who must enter the sterile field, and to minimize the tasks, such as holding a retractor, of personnel during surgical procedures. Further, it is desirable to have available to the surgeon instruments appropriately adapted to each type of procedure.

Coronary Bypass Surgery: The Midsternotomy

Coronary bypass surgery, in which the internal mammary artery is harvested from the chest wall and used for anastomosis of a vessel to bypass poorly functioning coronary arteries, has been performed thousands of times and has become an almost routine procedure for cardiac surgeons. Since the inception and throughout the development of the procedure, coronary bypass surgery has required a midsternotomy to provide access to the heart and coronary arteries. In the midsternotomy, an initial incision is made from the manubrium of the sternum to a point toward the xiphoid. Next, the sternum is split down the middle by means of a reciprocating sternal saw in order to provide access to the coronary arteries and the internal mammary artery. It has been estimated that in 1988, some 350,000 midsternotomy procedures were performed for coronary bypass surgery.

In performing the coronary bypass procedure, following the midsternotomy, it is necessary to retract one side of the split sternum in order to gain access to the thoracic cavity, and particularly to the internal mammary artery. Either the left or right internal mammary artery may be harvested for the bypass, so either side of the chest may need to be retracted. Retractors have been developed in order to provide the requisite retraction of the split sternum. An early example is disclosed in U.S. Pat. No. 4,622,955. The RULTRACT® internal mammary artery retractor is a more advanced retractor which has been developed to provide left or right internal mammary artery exposure in the undersurface of the chest wall. The RULTRACT® internal mammary retractor has been extensively used in coronary bypass surgery. The RULTRACT® retractor is not limited to coronary bypass surgery, having been used in various other thoracic surgical procedures, such as lung reduction and pericardial drainage.

The RULTRACT® internal mammary retractors include a rake plate and two or possibly three rakes. Most frequently, in use the two rakes are applied to one side of the opening formed by a midsternotomy and the rake plate is attached to a lifting device. The lifting device lifts the rake plate and the rakes, applying an upward and outward retraction to the sternum by which the surgical cavity is opened. The sternum is securely held in the open position when the lifting device is locked in position. This exposes the entire course of the mammary artery from its origin to its bifurcation, allowing its dissection. The rakes in the conventional retractor have a relatively small radius of curvature and have quite sharp tips to provide a secure attachment to the sternum. With the sternum securely held in the open position, the coronary artery dissection may then be carried out by the surgeon. In the standard midsternotomy, the retractor provides good exposure and allows the surgeon sufficient access for the dissection of the mammary artery.

After the coronary artery has been harvested, the RULTRACT® retractor is removed and a sternal retractor is placed in the chest and the grafting and anastomoses is performed. Closure is normally accomplished in this procedure by applying wires or staples to the sternum to hold it together in the properly aligned position for healing.

The midsternotomy is a highly invasive procedure, and much of the difficulty in recovering from a coronary surgical procedure involving a midsternotomy is due to the trauma resulting from the midsternotomy rather than to any trauma inflicted upon the coronary arteries or other thoracic organs and structures. As a result, a need has been identified for a less invasive procedure which will provide the surgeon with access to the coronary and internal mammary arteries with a minimum of trauma to the thoracic region.

The Mid-Cab. A Less Invasive Procedure

A less invasive procedure which has been developed to provide access to the mammary artery and the coronary arteries for coronary bypass surgery is known as the mid-cab or minimally invasive technique. In the mid-cab, an incision is made between the third and fourth rib, in the third intercostal region. The fourth rib is released from the sternum, and the incision is retracted downward by attaching a retractor rake to the fourth rib. A second retractor rake is next attached to the third rib, which is retracted upward and in the cranial direction. With access thus provided to the third rib and in the direction of the upper chest, the surgeon is able to create an opening from the third rib to the first rib or subclavian region. Via this opening, the surgeon is provided with access to the mammary artery, which is progressively dissected from the chest wall as the opening is progressively advanced toward the first rib. With the development of this procedure, a need has been identified for more advanced retractors specially adapted to the mid-cab procedure, and particularly for a retractor which can simultaneously retract the third and fourth ribs in different directions.

It is well known among cardiac surgeons that the position of the internal mammary artery in the chest is variable from patient to patient. For this reason, during the mid-cab procedure, it is sometimes necessary for the surgeon to manipulate the chest wall to provide adequate access to the mammary artery. The surgeon may have to either elevate or depress the chest wall in the region of the first rib in order to gain access to the mammary artery so that it can be dissected in this procedure. Thus, a need has been identified for devices which can assist the surgeon in the less invasive mid-cab procedure, particularly including a retractor capable of two-direction retraction at the site of the intercostal incision and devices for providing elevation and/or depression of the clavicle and first rib region of the chest wall.

In the device of U.S. Pat. No. 4,622,955 plural rakes which engage the body and retract the surgical cavity formed by a midsternotomy are relatively fixedly positioned with respect to each other from a rod. The rod may be elevated or lowered as desired. However, there is no adjustment for the rakes relative to the rod, to each other or to the surgical cavity. Furthermore, the rakes are generally small having sharply pointed tips and are generally designed to be employed in pairs for the purpose of retracting one side of a sternum which has been split by a midsternotomy. The device of U.S. Pat. No. 4,622,955 cannot provide the support required for other procedures which have been recently developed as alternatives to the midsternotomy approach to the coronary bypass, and it is not adapted for use in reoperative midsternotomy procedures.

It is well-known and appreciated that in surgical procedures, time is of the essence, and delays associated with adjustments of support equipment are unwanted. Additionally, during certain procedures, it may be desirable to impose or to change a biasing force on a body portion which is undergoing a surgical procedure or treatment. Further, it is desirable to minimize the number of personnel required to assist in the performance of a surgical procedure, to minimize the number of personnel who must enter the sterile field, and to minimize the tasks, such as holding a retractor, of personnel during surgical procedures. Further, it is desirable to have available to the surgeon instruments appropriately adapted to each type of procedure.

Reoperative Coronary Bypass Surgery

As coronary surgery has become increasingly prevalent and postoperative coronary rehabilitation more successful, a larger number of patients are surviving longer than the expected patency of their graft conduits. This has resulted in an increasing number of patients having to undergo a second coronary bypass procedure. The second, or reoperative, procedure has sometimes been referred to as a "re-do" procedure. Unfortunately, the re-do midsternotomy is neither as simple nor as safe as the initial procedure. This is primarily due to the scarring and resultant adhesions which develop between the internal side of the sternum and the underlying organs and tissues of the thoracic cavity following the initial midsternotomy. When the re-do midsternotomy is performed by essentially repeating the steps of the initial procedure, an increase in morbidity and mortality has been observed. Thus, a need has arisen for an alternative procedure.

An alternative procedure which has been adapted to coronary surgery in order to avoid the dangers of the re-do midsternotomy is known as a xiphoid entry. In the xiphoid entry, an initial incision is made along the scar from the previous midsternotomy to a point midway between the xiphoid and the umbilicus. The old sternal wires are removed. The xiphoid process is excised. A single retractor rake is applied to the caudal end of the sternum and the sternum is firmly retracted in an anterior and cranial direction. This allows the surgeon to directly visualize the anterior retrosternal space, so that the retrosternal adhesions can be taken down. The surgeon progressively takes down the adhesions toward the subclavian, until the sternum is freed from the underlying organs. Once this is done, the retractor may be removed and the sternum divided with a reciprocating sternal saw as in the original procedure.

During the retraction particular care must be exercised since, first, the quite sharp rake tips of the standard retractor are applied directly to the lower end of the sternum from which the xiphoid process was excised, and second, a very strong lifting force is required to elevate the entire sternum. The possibility of unintended trauma to the sternum exists. A second problem which has been experienced with the procedure described above is that the entire retractor plate and the extra, non-used rake must be suspended in a central location in the operating field, further obstructing the work area with its already limited space available. A third problem is that due to the rake plate and various parts attaching it to the lifting apparatus, the retraction force applied to the sternum is not transmitted in a simple straight line from the lifting apparatus to the sternum. Thus, a need has been identified for a rake which is more appropriately adapted to the xiphoid entry in a re-do coronary bypass procedure.

Accordingly, there is a strong need in the art to provide for surgical retractor apparatus with which to facilitate the development and implementation of new surgical procedures, particularly less invasive procedures such as the mid-cab coronary artery bypass procedure, and for more radical thoracic procedures such as a lung reduction or other procedure.

SUMMARY OF THE INVENTION

The internal mammary artery is known to thoracic surgeons to not have a well-defined position in all patients, but rather to have a highly variable position in the thoracic cavity. As a result, the procedure for accessing and harvesting a portion of the internal mammary artery must be quite flexible. This need is more pressing in a minimally invasive procedure such as in a mid-cab procedure. According to an aspect of the invention, a retraction device may be selected and quickly implemented as required in an individual surgical procedure depending on the particular patient's needs. The invention may allow the surgeon to perform a less-invasive procedure while maintaining the option to easily switch to the standard midsternotomy in the event of unforeseen difficulties. When the RULTRACT® retractor system and the device of the present invention are employed, the switch to the midsternotomy may be made with a minimum change of retraction equipment.

According to an embodiment of the present invention a surgical cable plate retractor includes a mounting plate having an attachment point at which the mounting plate is flexibly attached to a stationary support which includes a lifting device. The mounting plate includes a first pivotable portion which is pivotable relative to the attachment point, and a second fixed portion fixedly attached relative to the attachment point. The cable plate retractor of the present invention further may include at least one rake for applying a first retraction to the patient's body which is pivotably mounted with respect to the mounting plate. The cable plate retractor may include at least one cable plate assembly for applying retraction to a body at a position remote from the rake. The cable plate assembly may be mounted with respect to the mounting plate at a position remote from the rake. Such surgical retractor may further include means for adjusting the extension of the rake relative to the mounting plate. The surgical retractor of such embodiment may further include means for adjusting the extension of the cable plate relative to the mounting plate.

The surgical retractor has one rake attached to the first pivotable portion of the mounting plate, and a cable plate assembly attached to the second fixed portion of the mounting plate.

According to an embodiment of the present invention, the cable plate assembly preferably includes a plate, a cable, and means for retaining the cable relative to the assembly and the mounting plate and means for retaining the plate relative to the cable. More preferably, the cable plate assembly further includes means for adjusting the extension of the cable plate relative to the assembly and the mounting plate. The present invention preferably further includes a sleeve which may be placed over the cable plate. The sleeve makes the cable plate larger and provides a cushioning effect to avoid unnecessary trauma to the patient's body. The sleeve is preferably made of, or at least a portion of it includes, a non-metallic material. More preferably, the sleeve is made of, or at least a portion of it includes, a polymeric material. Most preferably, the sleeve is made of, or at least a portion of it includes, a relatively soft thermoplastic material.

The present invention further provides a surgical method for elevating a portion of a patient's body in order to hold open a surgical cavity. The method includes the steps of forming the surgical cavity by making a first surgical incision, placing a rake attached to a mounting plate relative to the cavity in a position for retraction, retracting a first portion of the patient's body, making a second surgical incision remote from the first incision and in communication with the surgical cavity, inserting a first end of a cable with a cable plate thereon into the surgical cavity, drawing the first end of the cable through the second body opening whereby the cable plate is retained in the patient's body at a second end of the cable, attaching the first end of the cable to the cable plate assembly, adjusting the position of at least one of the rake and the cable plate relative to the mounting plate, and retracting a second portion of the patient's body by lifting the cable plate. Preferably, the method includes the step of forming the second body opening by use of a trocar. Preferably, the method includes a step of placing a sleeve over the cable plate.

To the accomplishment of the foregoing and related ends, the invention then comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION

Figure 1:
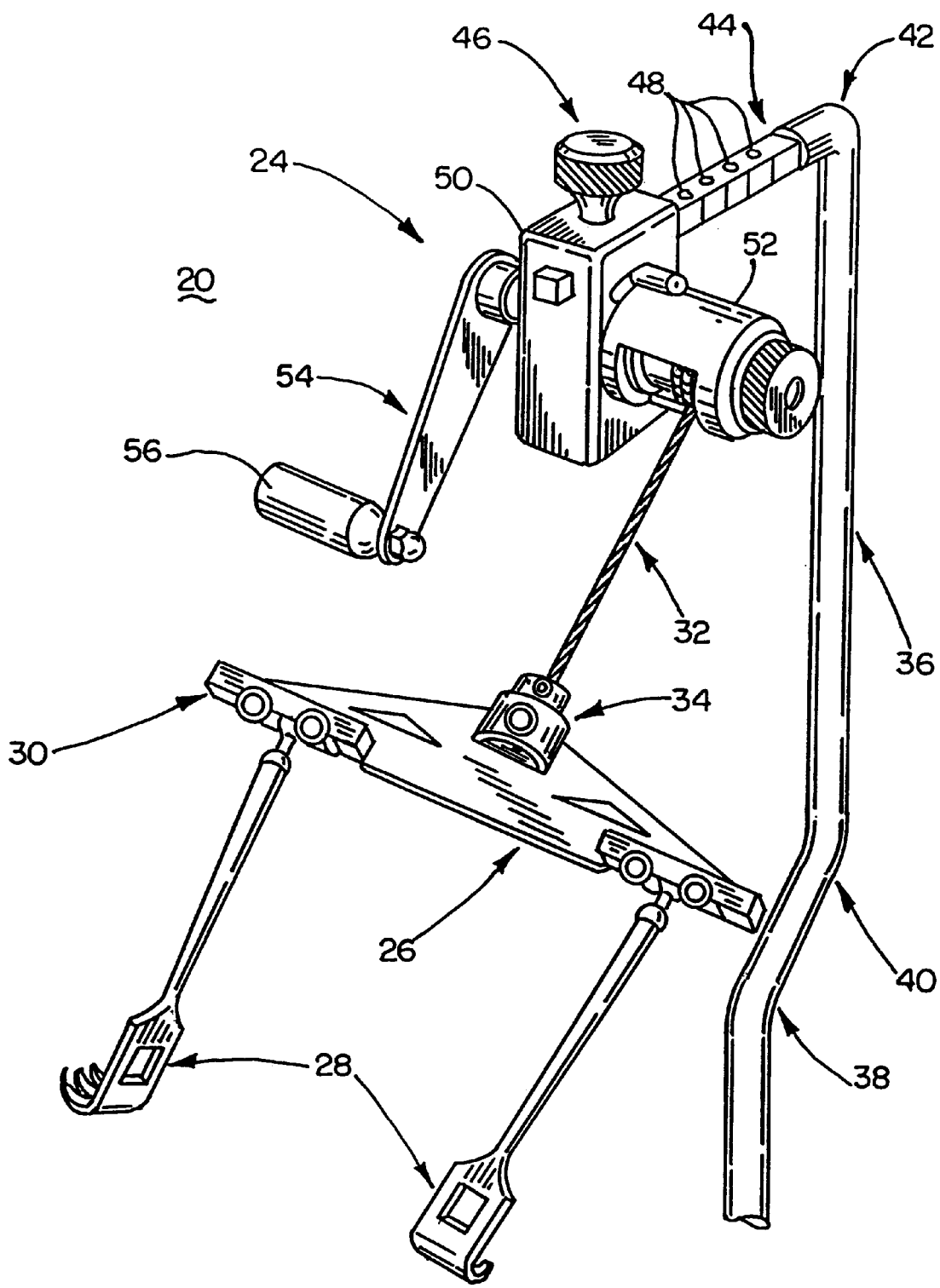
FIG. 1 is a perspective view of a conventional Rultract® surgical retractor.

The present invention will now be described with reference to the drawings wherein like reference numerals are used to refer to like elements throughout. As mentioned above, the present invention relates to surgical instruments for holding open a body part during surgery, for example, to maintain open and clear a surgical cavity during surgery, particularly including cardiac surgery or other thoracic surgery. In all embodiments described hereinafter, the preferred material of construction is stainless steel, preferably 304 stainless steel, which has good strength and sterilization characteristics and is resistant to corrosion even after many cycles of use, cleansing and sterilization. If desired, other materials having suitable characteristics for use in the invention may be employed.

Referring to FIG. 1, a conventional RULTRACT® retractor and surgical support assembly 20 are shown. The RULTRACT® retractor includes a ratcheting lifting device 24, a rake plate 26, at least one rake 28 for applying retraction to a patient's body, and pivoting mounting means 30 for mounting the rakes 28 to the rake plate 26. The rake plate 26 is attached to the ratcheting lifting device 24 by a cable 32. The cable 32 is attached to the rake plate 26 by a pivot hub connector 34.

The rake plate 26 and the rakes 28 associated therewith may be raised or lowered via the cable 32, which is connected to the ratcheting lifting device 24.

As described below, the RULTRACT® system preferably includes a ratcheting lifting device 24, although other lifting devices could be used. Preferably, a pivot hub connector 34 allows the rake plate 26 to rotate relative to the cable 32 to facilitate positioning of the rakes 28 relative to the surgical cavity of the patient without twisting the cable 32, which could result in a torque applied to the retractor rake plate 26, which undesirably could be transmitted to the patient's body.

In the conventional RULTRACT® retractor assembly 20, the ratcheting lifting device 24 is mounted on a support pole 36. Although not shown in FIG. 1, the support pole 36 is mounted at its lower end to a surgical table by conventional means. Preferably, the support pole 36 includes bends 38 and 40 which dispose outward the portion of the support pole 36 which is above the level of the surgical table so as to provide additional space in the surgical field around the patient. At the upper end of the pole 36, is a bend 42, preferably a right angled bend, connecting the support pole 36 to a horizontally extending portion 44. The horizontally extending portion 44 extends outwardly above the patient, so that the retraction force is applied at least partially in an upward direction. Since the lifting device 24 is not aligned with the patient's midline, the retraction is applied partially, outwardly, laterally with respect to the patient.

In this embodiment, the ratcheting lifting device 24 is mounted on the horizontal extension 44. The lifting device 24 is provided with a securing bolt 46 by which the lifting device 24 is securely positioned on the extension 44. To facilitate quick and sure positioning of the lifting device 24 on the extension 44, a plurality of bores 48 are provided, into which an end of the securing bolt 46 may be inserted. The bores 48 allow for precise horizontal adjustment of the position of the lifting device 24 relative to the patient and the surgical field.

The ratcheting lifting device 24 preferably includes a ratcheting winch assembly 50 for reeling in the cable 32. The cable 32 is attached to and preferably is wrapped around a spool (not shown) extending outwardly from the ratcheting winch assembly 50. The spool around which the cable 32 wraps is preferably partially enclosed by a housing 52. The opposite end of the spool is attached to, and the winching assembly is actuated by, the crank arm 54 and crank handle 56, in conventional fashion.

The lifting device and support arm used in the present invention are preferably essentially the same as the conventional assembly described above and will not be further described except as necessary to indicate the functioning of the present invention relative thereto. The conventional parts of the apparatus shown in FIG. 2 are indicated by reference numeral 58.

Figure 2:
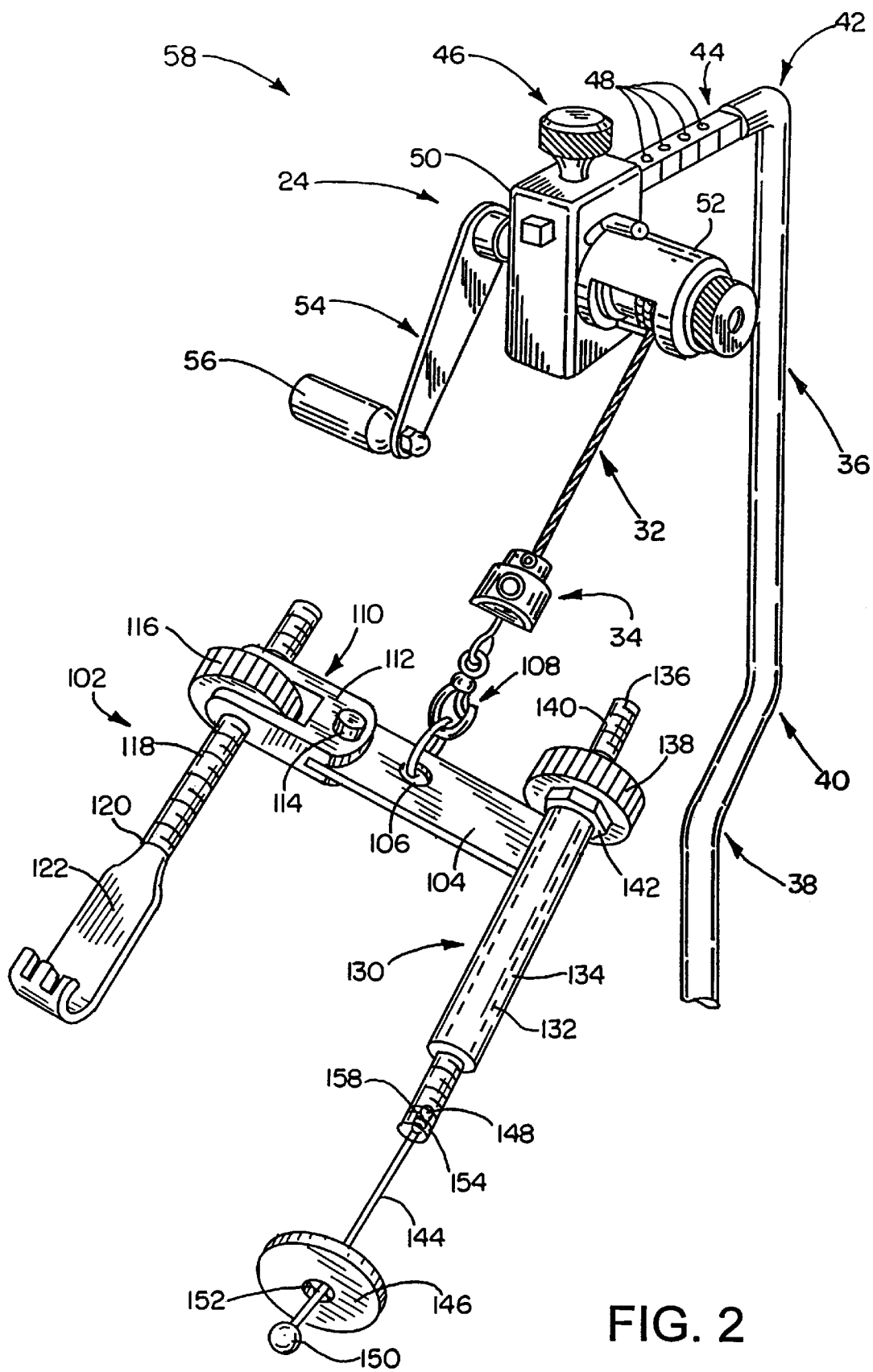
FIG. 2 is a perspective view of a retractor support and lifting apparatus including an embodiment of the present invention mounted thereon.

The present invention provides additional assistance to the surgeon in accessing the internal mammary artery while still allowing the surgeon to proceed to use a minimally invasive surgical procedure, and a complete retraction system employing the present invention is shown in FIG. 2. A cable plate retraction device 102, in accordance with the present invention, is shown in FIG. 2. The cable plate retractor 102 may be mounted on the conventional RULTRACT® retractor support system 58 described above, as shown in FIG. 2, or may be mounted on other support systems.

Figure 3:
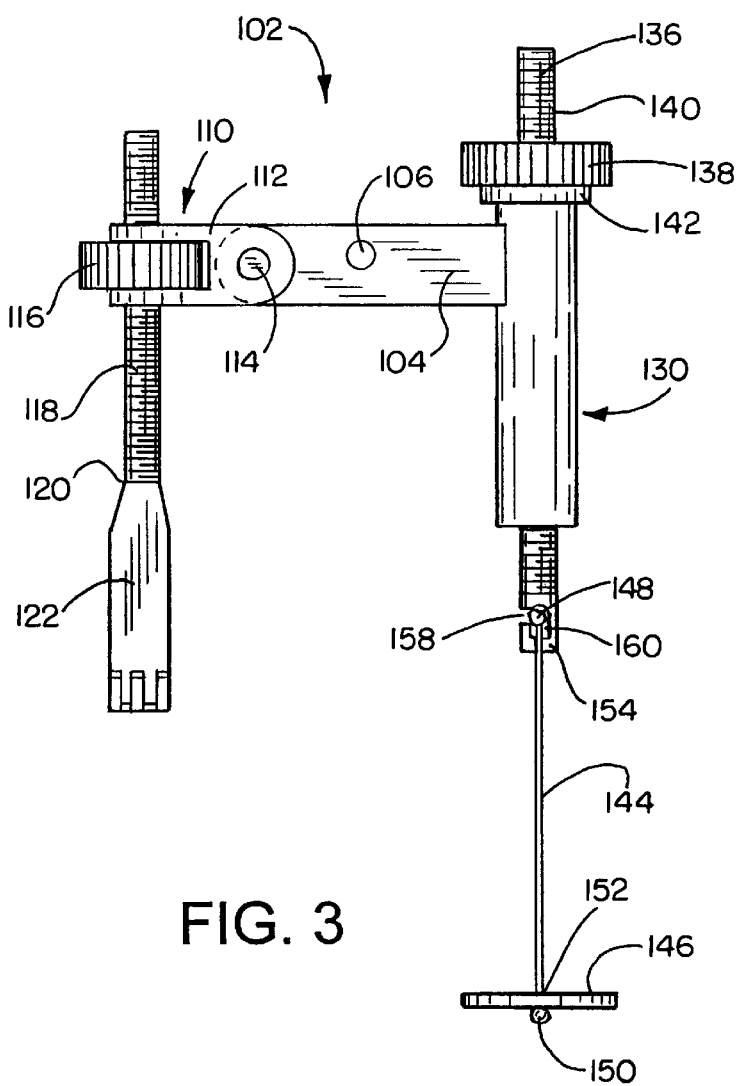
FIG. 3 is a schematic illustration of the cable plate retractor in accordance with the present invention.

The preferred cable plate retractor 102, shown in FIGS. 2 and 3, includes a central mounting plate 104, having an opening 106 for attaching to the ratcheting lifting device 24. The attachment to the lifting device 24 via the cable 32 and the pivot hub 34 at the opening 106 may be by any conventional means, but preferably includes a snap clip 108 in FIGS. 2 and 7. The snap clip 108 provides for quick and easy attachment or removal of the cable plate retractor 102. Other quick-release devices known in the art may be substituted for the snap clip 108.

As shown in FIGS. 2 and 3, the left-hand side of the cable plate retractor preferably comprises a pivotable adjustable rake arm 110. The arm 110 may be fixedly attached (not shown) or pivotably attached (as shown in the Figures) to the central mounting plate 104. In the pivotably attached embodiment the arm 110 comprises a pivot clamp 112, a pivot pin 114 for mounting the pivot clamp 112 on the mounting plate 104, a threaded nut 116 which threadingly mates with a threaded portion 118 of a shaft 120 of a rake 122. The threaded nut 116 may be operated in conjunction with the threaded portion 118 to adjust vertically the shaft 120 and thereby the rake 122. Thus, the pivoting mounting means 110 provides for vertical adjustment of the rake 122 by which its position may be adjusted relative to the mounting plate 104. The pivot clamp 112 is allowed to move in a swiveling or pivoting motion about the pivot pin 114 relative to the mounting plate 104 by which the angle of the pivot clamp 112 and thereby the rake 122 may be adjusted with respect to the central mounting plate 104.

The right-hand portion of FIGS. 2 and 3 shows a cable plate assembly 130 of the cable plate retractor 102. The cable plate assembly 130 includes a cable plate mounting tube 132. The mounting tube 132 is preferably fixedly mounted to the mounting plate 104, but may be mounted in a pivotable fashion such as that shown and described for the adjustable rake arm 110. The mounting tube 132 preferably includes an interior passage 134 extending along its entire length, thus providing an opening therethrough. Preferably, the interior passage 134 is cylindrical, but it may have any convenient configuration.

In the assembled cable plate retractor 102, a threaded shaft 136 passes through the passage 134. At the upper end of the threaded shaft 136 is mounted a threaded nut 138 which, like the threaded nut 116 and the shaft 118, threadingly mates with threads 140 on the shaft 136. Rotation of the threaded nut 138 thus provides for vertical movement of the threaded shaft 136 with respect to the mounting tube 132 of the cable plate assembly 130. Preferably, the threaded nut 138 includes an integral bearing surface 142 which bears directly upon the upper end of the mounting tube 132. In alternative embodiments, some other bearing device, such as a washer, may be provided between the threaded nut 138 and the upper end of the mounting tube 132.

Figure 4:
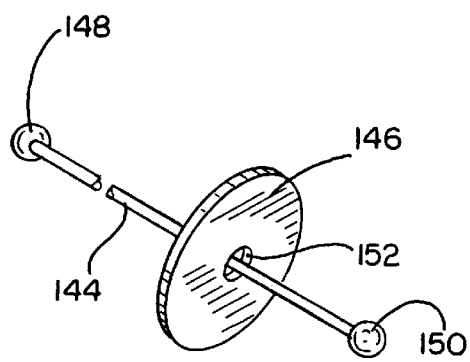
FIG. 4 is a side perspective view of a cable and lifting plate such as used in the present invention.

The lower end of the threaded shaft 136 preferably includes a mounting for a cable 144, upon which a lifting plate 146 is mounted. As shown in FIG. 4, the cable 144 preferably has enlarged ends 148 and 150, which are larger relative to the diameter of the cable 144. Similarly, the ends 148, 150 are larger than the central opening 152 in the lifting plate 146 so as to provide retention of the mounting plate 146 on the cable 144. Similarly, the ends 148, 150 are larger than the shoulder 154 as described below, so that the cable 144 is retained on the threaded shaft 136. As shown in FIG. 2, the lifting plate 146 includes a central hole 152 which is slightly larger in diameter than is the cable 144 but smaller than the cable ends 148, 150. This allows the lifting plate 146 to move freely along the cable, but to be retained permanently thereon. Preferably, the lifting plate 146 is circular and is symmetrical with respect to its upper and lower surfaces.

As shown in FIG. 2, at the lower end of the threaded shaft 136 is provided a mounting slot 158 for mounting the cable 144 in the shaft 136. The mounting slot 158 is large enough to allow either of the enlarged ends 148, 150 to pass freely for insertion into the slot 158. As described above and shown in FIG. 4, preferably the enlarged ends 148, 150 are identical and the cable 144 is thus symmetrical, so that either end 148 or 150 may be inserted into the slot 158 to equal effect.

Figure 6:
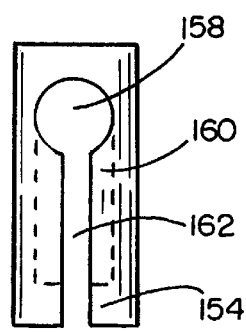
FIG. 6 is a partial detail of a side elevational view of a slot portion of the embodiment shown in FIGS. 3 and 5, prior to insertion of a cable.

As shown best in FIG. 6, the slot 158 communicates with a vertical passage 160 within the shaft 136. The vertical passage 160 has a diameter sufficiently large to allow the enlarged ends 148, 150 to pass freely through its length to the shoulder 154. Preferably, the passage 160 communicates with a vertical slot-like opening 162 which is large enough to allow the cable 144 to pass therethrough, but is sufficiently small enough to prevent either enlarged end 148, 150 to pass therethrough. At the lower end of and inside the passage 160 is the shoulder 154 which has a diameter smaller than the ends 148, 150, but larger than the cable 144, and upon which the enlarged end 148 (or 150) of the cable 144 will rest when the cable 144 is inserted and drawn downwardly in the passage 160. Preferably, the diameter of the passage formed by the shoulders 154 is approximately equal to the width of the vertical opening 162 and slightly larger than the thickness or diameter of the cable 144.

Figure 5:
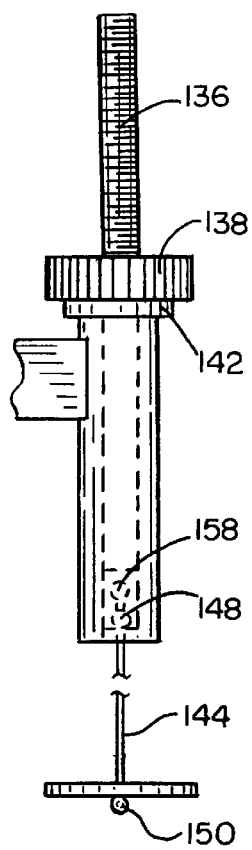
FIG. 5 is a partial detail of a side elevational view of a cable plate assembly of the embodiment shown in FIG. 3, with the cable in position for retracting.

The cable 144 and the end 148, when inserted in the slot 158 and passage 160 and urged downwardly against the shoulder 154, are preferably centrally disposed with respect to the shaft 136. With the cable 144 in position, the threaded nut 138 can be rotated so as to draw the lower end of the shaft 136, along with its opening 158, into the interior passage 134 of the tube 132. As a consequence, the enlarged end 148 (or 150) of the cable 144 is securely retained within the tube 132 of the cable plate retractor 102, as shown in FIG. 5.

Figure 8:
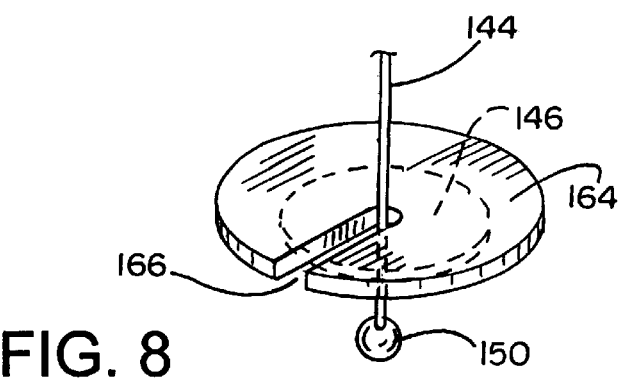
FIG. 8 is a perspective view of a cable and lifting plate with a sleeve in place, in accordance with the invention.

As schematically shown in FIG. 8, the present invention preferably further includes a sleeve 164 which may be placed over the cable plate 146. The sleeve 164 makes the cable plate 146 larger so that the retraction force is applied over a larger area and the resulting pressure on the patient's body is correspondingly reduced. The sleeve 164 may also provide a cushioning effect to further avoid unnecessary trauma to the patient's body. The sleeve 164 preferably includes a slot 166 through which the cable 144 can pass, to provide for placing the sleeve 164 on the unit formed by the cable 144 and the lifting plate 146. Preferably, the slot 166 is just large enough to allow the cable to be pushed through the slot, so that the size of the slot assists in retaining the sleeve 164 on the unit formed by the cable 144 and the lifting plate 146. The sleeve 164, as shown in FIG. 8, is fractionally larger than the lifting plate 146. However, it is recognized that the sleeve may be as large as deemed by the surgeon necessary to avoid unnecessary trauma to the patient's body.

The sleeve 164 is preferably made of, or at least a portion of it includes, a non-metallic material, more preferably is made of, or at least a portion of it includes, a polymeric material, and most preferably is made of, or at least a portion of it includes, a relatively soft thermoplastic material.

The sleeve 164 may be entirely formed of the non-metallic material, or, as required, it may include a metallic portion and a non-metallic portion. For example, if the lifting plate 146 has a relatively small diameter, a sleeve may have a metal portion with a diameter somewhat larger than the lifting plate 146 and a non-metallic portion of a diameter significantly larger than the metal portion of the sleeve. Such an arrangement would provide a large total lifting area, but would allow the lifting plate 146 to be as small as possible.

The cable 144 may have a variety of lengths, and the surgeon may select the appropriate length for a particular patient. The cable 144 and the lifting plate 146 may be provided as a disposable unit, as may the sleeve 164 similarly be disposable.

Figure 7:
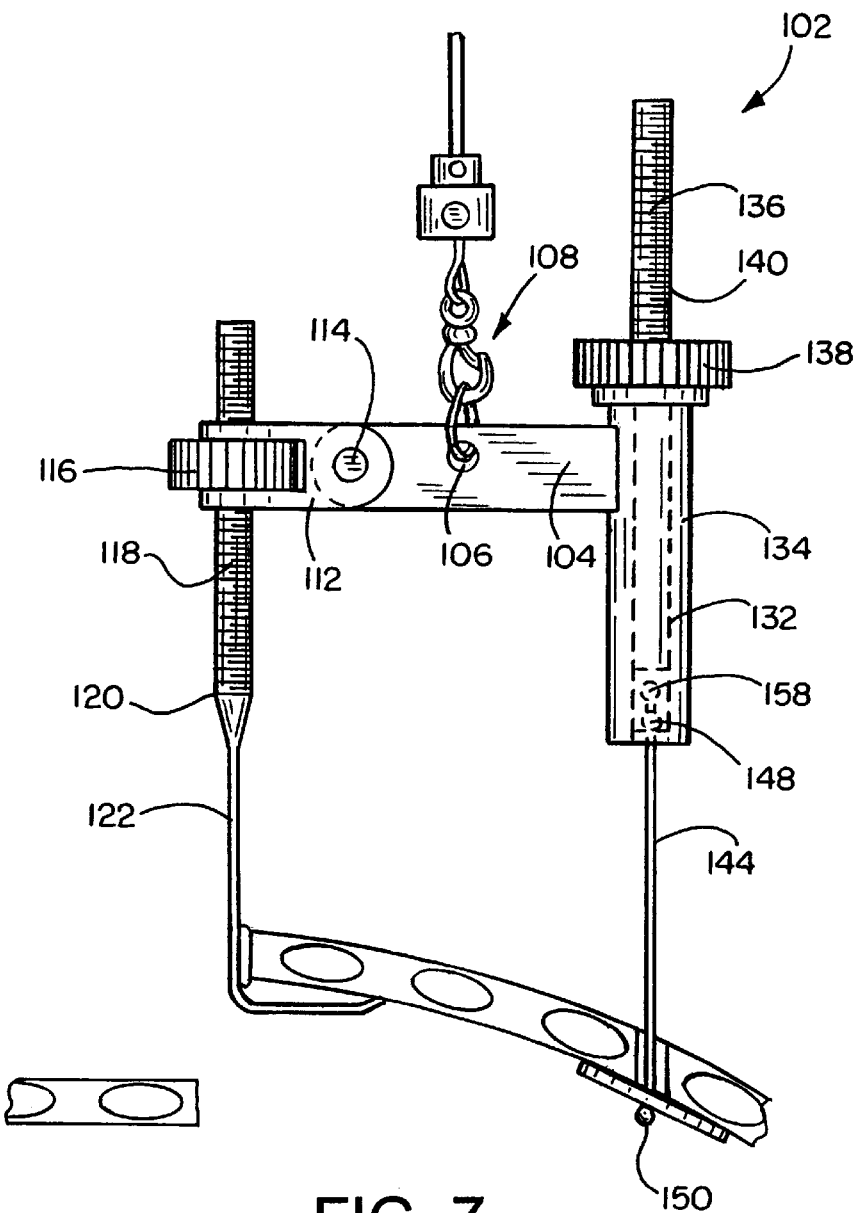
FIG. 7 is a schematic partial cutaway side elevational view of the cable plate retractor of the present invention in use in a patient's body during a midcab surgical procedure.

A surgical method for retracting a portion of a patient's body in order to hold open a surgical cavity, using the cable plate retractor 102, for example, as is shown schematically in FIG. 7, will now be described. It is to be recognized that the method described is illustrative of how the device may be used and is exemplary only. The method includes at least the following steps. A first body opening or surgical cavity is provided by standard surgical techniques, for example in a mid-cab procedure, by making an incision in the third or fourth intercostal region. The next step is placing a rake, attached to a cable plate assembly and a retraction system, relative to the surgical cavity, for example in a position to elevate the patient's third rib, adjacent the incision in the third intercostal region. The rake may be lifted so as to retract the rib, or other body portion, and provide access to the patient's thoracic cavity, in which the surgeon can divide the tissues therein, preferably the internal mammary artery, from the patient's rib cage. The next step in the method is forming a second surgical incision in the patient's body at a position remote from the first incision and in communication with the surgical cavity. The second body opening is preferably made by means of a trocar, and in a mid-cab procedure may be made in a location near the patient's first rib or clavicle. The surgeon may then insert a first end of the cable with its cable plate mounted thereon, and optionally a sleeve mounted thereon, into the first body opening or surgical cavity. The surgeon draws the first end of the cable through the second surgical incision. When the cable end appears through the opening outside the patient's body, the surgeon draws the cable up through the second body opening. Since the cable plate is too large to pass through the second surgical incision, it is retained in the patient's body at the second end of the cable. Next, the surgeon attaches the first end of the cable to the cable plate assembly, by passing the enlarged end of the cable through a slot in the shaft of the cable plate assembly. Next, the position of the cable plate may be adjusted relative to the mounting plate, and the position of at least one of the rake and the cable plate may be further adjusted relative to the cable plate assembly. Finally, a second portion of the patient's body may be retracted, together with or separately from the first portion of the patient's body, by means of the retraction force applied to the cable plate.

By means of the foregoing method, the surgeon may be provided with access to a very large surgical cavity in the patient's thoracic cavity by making only a single surgical opening of significant size and one very small second surgical opening. If this method was not available, the surgeon might be required to make two surgical openings of significant size, or to split the sternum in a midsternotomy which of course creates a very large surgical incision. The present procedure allows the surgeon to elevate, e.g., both the area of the third intercostal region and the region of the clavicle and first rib when necessary to provide access to the patient's internal mammary artery, in a coronary bypass procedure including the less invasive mid-cab incision.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

What is claimed is:

1. A cable plate retractor assembly comprising:
   a central mounting plate having a flexible attachment to a lifting device;
   at least one rake mounted with respect to the mounting plate for applying a first retraction to a patient's body; and
   at least one cable plate assembly mounted with respect to the mounting plate spaced from the at least one rake for applying a second retraction to the patient's body at a position remote from the rake.

2. A retractor assembly as in claim 1, wherein the mounting plate further includes a pivotable portion pivotably mounted relative to the attachment and said at least one rake is attached thereto.

3. A retractor assembly as in claim 1, wherein the mounting plate further includes a pivotable portion pivotably mounted relative to the attachment and said at least one cable plate assembly is attached thereto.

4. A retractor assembly as in claim 1, wherein said at least one rake is fixedly attached to the mounting plate.

5. A retractor assembly as in claim 1, wherein said at least one cable plate assembly is fixedly attached to the mounting plate.

6. A cable plate retractor assembly comprising:
   a central mounting plate having a flexible attachment to a lifting device;
   at least one rake mounted with respect to the mounting plate for applying a first retraction to a patient's body; and
   at least one cable plate assembly mounted with respect to the mounting plate spaced from the at least one rake for applying a second retraction to the patient's body at a position remote from the rake,
   and further comprising means for adjusting the extension of said at least one rake relative to the mounting plate.

7. A cable plate retractor assembly comprising:
   a central mounting plate having a flexible attachment to a lifting device;
   at least one rake mounted with respect to the mounting plate for applying a first retraction to a patient's body; and
   at least one cable plate assembly mounted with respect to the mounting plate spaced from the at least one rake for applying a second retraction to the patient's body at a position remote from the rake,
   wherein said at least one cable plate assembly comprises a cable and a lifting plate retained on the cable.

8. A retractor assembly as in claim 7, further comprising means for adjusting the extension of the cable relative to the mounting plate.

9. A retractor assembly as in claim 7, wherein the lifting plate has an opening sized to receive the cable therethrough and allow the lifting plate to move freely along the cable.

10. A retractor assembly as in claim 7, further including means for retaining the cable relative to the mounting plate.

11. A retractor assembly as in claim 7, where in said at least one cable plate assembly further comprises means for adjusting the proximity of the lifting plate relative to the mounting plate.

12. A cable plate retractor assembly comprising:
    a central mounting plate having a flexible attachment to a lifting device;
    at least one rake mounted with respect to the mounting plate for applying a first retraction to a patient's body; and
    at least one cable plate assembly mounted with respect to the mounting plate spaced from the at least one rake for applying a second retraction to the patient's body at a position remote from the rake,
    wherein said at least one cable plate assembly further comprises a sleeve.

13. A retractor assembly as in claim 12, wherein the sleeve comprises a non-metallic material.

14. A retractor assembly as in claim 12, wherein the sleeve comprises a polymeric material.

15. A surgical method for retracting a portion of a patient's body in order to hold open a surgical cavity, comprising the steps of:
    forming the surgical cavity by making a first surgical incision;
    placing a rake attached to a mounting plate relative to the surgical cavity in a position for retraction;
    providing means for adjusting the extension of the rake relative to the mounting plate;
    retracting a first portion of the patient's body;
    making a second surgical incision in the patient's body at a position remote from the first incision and in communication with the surgical cavity;
    inserting a first end of a cable with a lifting plate thereon into the surgical cavity;
    drawing the first end of the cable through the second surgical incision whereby the lifting plate is retained in the patient's body at a second end of the cable;
    providing means for adjusting the extension of the cable relative to the mounting plate;
    adjusting the position of at least one of the rake and the lifting plate relative to the mounting plate; and
    retracting a second portion of the patient's body by raising the lifting plate.

16. A method according to claim 15 wherein the step of making a second surgical incision is performed using a trocar.

17. A method according to claim 15 further including the step of placing a sleeve on the lifting plate.

18. A surgical method for retracting a portion of a patient's body in order to hold open a surgical cavity, comprising the steps of:
    forming the surgical cavity;
    making a surgical incision in the patient's body in communication with the surgical cavity;
    inserting a first end of a cable with a lifting plate thereon into the surgical cavity;
    drawing the first end of the cable through the surgical incision whereby the lifting plate is retained in the patient's body at a second end of the cable;
    adjusting the position of the lifting plate relative to a mounting plate; and
    retracting a portion of the patient's body by raising the lifting plate.

19. A method according to claim 18 further comprising the steps of:
    placing a rake attached to a mounting plate relative to the surgical cavity in a position for retraction;
    providing means for adjusting the extension of the rake relative to the mounting plate;
    adjusting the position of the rake relative to the mounting plate; and
    retracting a portion of the patient's body by raising the rake.

20. A cable plate retractor assembly comprising:

a central mounting plate having a flexible attachment to a lifting device;

at least one rake mounted with respect to the mounting plate for applying a first retraction to a patient's body; and at least one cable plate assembly mounted with respect to the mounting plate spaced from the at least one rake for applying a second retraction to the patient's body at a position remote from the rake, wherein said at least one cable plate assembly further comprises a lifting plate.

21. A lifting assembly for use with a surgical patient comprising:

an elongate relatively flexible member, the flexible member being connectable relative to a support;

a plate member positionable relative to the surgical patient, the plate member being mountable on the flexible member at a position distal to the support;

wherein the plate member, when positioned relative to the surgical patient, may provide lift to a body portion of the surgical patients, further comprising a sleeve mountable upon the plate member.

22. A lifting assembly as in claim 21, wherein the plate member includes a centrally disposed opening for mounting on the flexible member.

23. A lifting assembly as in claim 21, wherein the plate member is circular.

24. A lifting assembly as in claim 21, wherein the flexible member is a cable.

25. A lifting assembly as in claim 21, further comprising a sleeve mountable upon the plate member.

26. A lifting assembly for use with a surgical patient comprising:

an elongate relatively flexible member, the flexible member being connectable relative to a support;

a plate member positionable relative to the surgical patient, the plate member being mountable on the flexible member at a position distal to the support;

wherein the plate member, when positioned relative to the surgical patient, may provide lift to a body portion of the surgical patient, and the assembly includes an adjustment mechanism to move the plate relative to the support, wherein the mechanism to move the plate includes a threaded member.

27. A lifting assembly as in claim 26, wherein the support further comprises a socket for removably connecting to the flexible member.

28. A lifting assembly as in claim 26, wherein the mechanism to move the plate includes a threaded member.

29. A lifting assembly as in claim 26, wherein the support includes a mounting tube and the threaded member is movable within the tube.

30. A lifting assembly as in claim 26, wherein the threaded member is operably coupled to a threaded nut.

31. A cable plate retractor assembly comprising:

central mounting means for flexible attachment to a lifting means;

at least one rake means mounted with respect to the mounting means for applying a first retraction to a patient's body; and at least one cable plate means mounted with respect to the mounting means spaced from the at least one rake means for applying a second retraction to the patient's body at a position remote from the rake means, wherein said at least one cable plate means further comprises a lifting plate means for applying the second retraction.

32. A lifting assembly for use with a surgical patient comprising:

an elongate relatively flexible means being connectable to a support;

a plate means positionable relative to the surgical patient for providing lift to a body portion of the surgical patient;

wherein the plate means is mountable on the flexible member at an end distal from the support when positioned relative to the surgical patient, wherein the assembly further comprises a sleeve mounted on the support.

33. A lifting assembly for use with a surgical patient comprising:

an elongate relatively flexible means being connectable to a support means;

a plate means positionable relative to the surgical patient, for providing lift to a body portion of the surgical patient, wherein the plate means is mountable upon an end of the flexible means distal from the support means; and wherein the assembly includes threaded means for adjusting the lift by moving the plate means relative to the support means.

* * * * *